United States Patent
Ikhlef et al.

(10) Patent No.: US 8,121,248 B2
(45) Date of Patent: *Feb. 21, 2012

(54) X-RAY DETECTOR METHODS AND APPARATUS

(75) Inventors: Abdelaziz Ikhlef, Waukesha, WI (US); Charles Hugh Shaughnessy, Whitefish Bay, WI (US)

(73) Assignee: General Electric Company, Schenectady, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 12/908,297

(22) Filed: Oct. 20, 2010

(65) Prior Publication Data

US 2011/0091009 A1 Apr. 21, 2011

Related U.S. Application Data

(63) Continuation of application No. 11/551,019, filed on Oct. 19, 2006, now Pat. No. 7,869,559.

(51) Int. Cl.
*A61B 6/00* (2006.01)

(52) U.S. Cl. ............ 378/5; 378/19; 378/98.8; 378/98.9

(58) Field of Classification Search ............... 378/5, 19, 378/98.8, 98.9
See application file for complete search history.

(56) References Cited

U.S. PATENT DOCUMENTS

| | | |
|---|---|---|
| 4,392,235 A | 7/1983 | Houston |
| 4,637,040 A | 1/1987 | Sohval et al. |
| 5,499,283 A | 3/1996 | Toki |
| 5,570,403 A | 10/1996 | Yamazaki et al. |
| 5,841,832 A | 11/1998 | Mazess et al. |
| 6,041,097 A | 3/2000 | Roos et al. |
| 6,128,365 A | 10/2000 | Bechwati et al. |
| 6,428,206 B1 | 8/2002 | Watanabe |
| 6,473,486 B2 | 10/2002 | Hoffman |
| 6,480,562 B2 | 11/2002 | Jiang et al. |
| 6,480,563 B2 | 11/2002 | Hoffman et al. |
| 6,528,795 B2 | 3/2003 | Kurfess et al. |
| 6,553,096 B1 | 4/2003 | Zhou et al. |
| 6,654,443 B1 | 11/2003 | Hoffman |
| 6,704,391 B2 | 3/2004 | Hoffman et al. |
| 6,735,274 B1 | 5/2004 | Zahavi et al. |
| 6,775,348 B2 | 8/2004 | Hoffman |
| 6,891,166 B2 | 5/2005 | Brahme et al. |
| 7,092,481 B2 | 8/2006 | Hoffman |
| 7,233,640 B2 | 6/2007 | Ikhlef et al. |
| 7,492,855 B2 | 2/2009 | Hopkins et al. |
| 7,778,383 B2 | 8/2010 | Koehler et al. |
| 7,869,559 B2 * | 1/2011 | Ikhlef et al. ............ 378/5 |
| 2004/0234031 A1 * | 11/2004 | Francke et al. ............ 378/98 |
| 2005/0056829 A1 | 3/2005 | Green et al. |
| 2009/0147910 A1 | 6/2009 | Edic et al. |

* cited by examiner

*Primary Examiner* — Hoon Song
*Assistant Examiner* — Mona M Sanei
(74) *Attorney, Agent, or Firm* — Ziolkowski Patent Solutions Group, SC

(57) ABSTRACT

A method includes performing an x-ray focal spot deflection to generate two complete projections from two different channels of an x-ray detector, wherein the channels are purposefully different from each other in some respect other than being different channels.

20 Claims, 3 Drawing Sheets

X-RAY DETECTOR METHODS AND APPARATUS

CROSS-REFERENCE TO RELATED APPLICATION

The present application is a continuation of, and claims priority to, U.S. non-provisional application Ser. No. 11/551,019, filed Oct. 19, 2006.

BACKGROUND OF THE INVENTION

This invention relates generally to a diagnostic imaging method and apparatus, and more particularly, to a method and apparatus that provide detectors that are useful in computed tomography (CT).

Most multi-slice CT scanners are built with detectors composed of scintillator/photodiodes arrays. The photodiodes arrays are mainly based on front-illuminated technology. However, new designs based on back-illuminated photodiodes are being developed for CT machines to overcome the challenge of the higher number of runs and connection required. Current CT detectors generally use scintillation crystal/photodiode arrays, where the scintillation crystal absorbs x-rays and converts the absorbed energy into visible light. A photodiode is used to convert the light to an electric current. The electric current is read and the reading is proportional to the total energy absorbed. In these designs, the signal detected by the diode represents the integrated energy of the x-ray flux, during a short period of time, without any discrimination of energy.

Recently new ideas of CT detectors are being investigated for energy discrimination purposes using particularly direct conversion x-ray detector (or photoconductor) material such as CZT, CdTe, PbO, and etc., material based photo-detectors. In this document, all direct conversion x-ray detectors are referred to as direct conversion material (CDM) detectors. These detectors are capable of photon counting and then measuring the energy of every photon. However, there is still a major challenge to overcome in order to achieve good CT performance and quality. Most of these detectors, working in photon counting modes are limited in their counting rate, either by pile-up effect, saturation, dynamic range, etc.

Besides, these detectors typically saturate at relatively low x-ray flux levels, which makes the detector feasible only in very low flux conditions. Therefore, described below is a detector which can be used in high x-ray flux environments. One way to overcome this limitation (limited count rate) is to find a method to provide energy information using integrating detectors such as in conventional CT systems. For this purpose, dual KVp systems can respond to the need because they do not suffer from count-rate limitations, as they typically used conventional detectors, operating in integrating mode. However, since the two data sets are acquired some distance apart in space or in time, this approach will be limited in its ability to resolve rapid changes in anatomy due to organ motion. When combined with a data acquisition system which is capable of resolving the energy of individual photon events, the system provides energy information which is not available in conventional CT. The advantage is that the energy information is provided simultaneously which enables the avoidance of motion related errors.

The proposed invention provides energy discrimination by interleaving data channels with different spectral responses. The combination of a) interleaving of channels having different spectral sensitivities and b) focal spot deflection will lead to a CT system with two or several images at different x-ray energies, or spectral windows. This patent describes the different ways of achieving detectors with different spectral responses.

BRIEF DESCRIPTION OF THE INVENTION

In one aspect, a method includes performing an x-ray focal spot deflection to generate two complete projections from two different channels of an x-ray detector, wherein the channels are purposefully different from each other in some respect other than being different channels.

In another aspect, a computer is configured to perform an x-ray focal spot deflection, and receive data forming two complete projections from two different channels of an x-ray detector, wherein the channels are purposefully different from each other in some respect other than being different channels.

In yet another aspect, a system is provided. The system includes an x-ray source, and an x-ray detector positioned to receive x-rays emitted from the source; wherein the detector includes at least two channels wherein the channels are purposefully different from each other in some respect other than being different channels.

BRIEF DESCRIPTION OF THE DRAWINGS

FIG. 3 illustrates a detector with a CDM detector portion and a scintillator portion.

FIG. 4 illustrates a detector with different thicknesses of scintillator material.

FIG. 5 illustrates a detector with a metallic or any absorptive filter on every other channel.

DETAILED DESCRIPTION OF THE INVENTION

There are herein described methods and apparatus useful for imaging systems such as, for example, but not limited to an x-ray system. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention. More particularly, herein described is a detector that enables the acquisition of x-ray images with different spectral contents using two different types of pixels (channels), wherein the channels are purposefully different from each other in some respect other than being different channels. The combination of this detector with focal spot deflection or an interpolation algorithm leads to an acquisition of two projections (images) of different spectral contents without losing the spatial resolution or image quality.

Herein described are methods and apparatus that enable the measurement of x-rays through two different mechanisms. In one embodiment, a detector is provided where the channels have different spectral properties and are interleaved in the channel direction (in the plane or the x-direction). In order to have a full set of data to reconstruct the images, one can imagine switching (deflecting) the focal spot in the channel direction by an equivalent distance of a cell (channel) from view to view (in time domain) or other algorithm based on interpolation between channels and slices. In this case, the projection data from each detector type can be acquired during one full rotation with the desired x-direction resolution. Some known systems employ focal spot position switching, for example, see U.S. Pat. No. 4,637,040.

Figure 1:
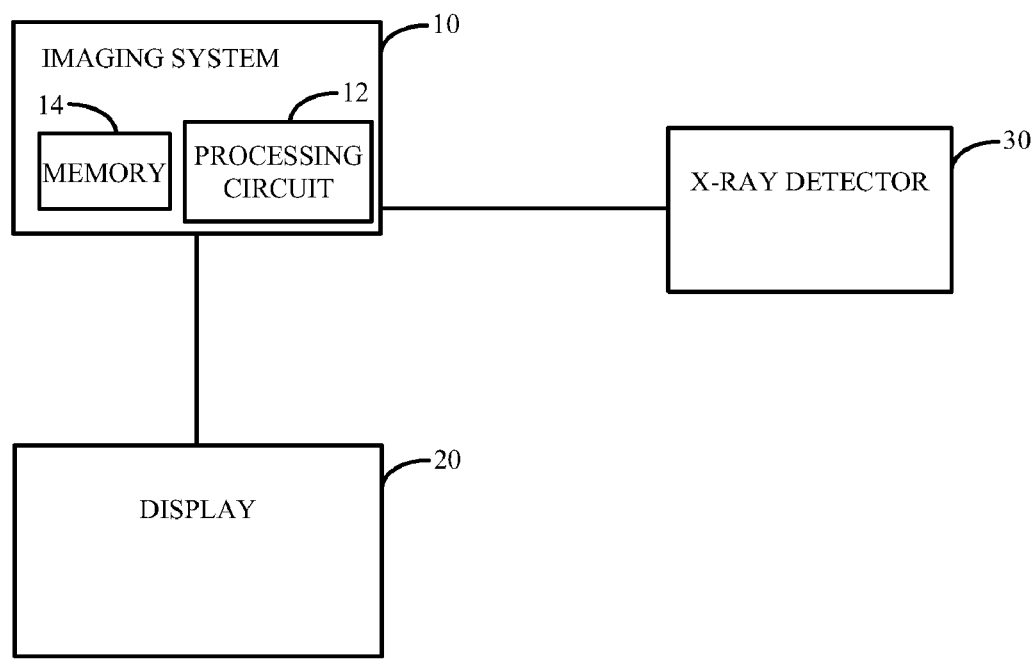
FIG. 1 illustrates a computed tomography system.

FIG. 1 illustrates an imaging system 10 with an associated display 20. Imaging system 10 can be of any modality, but in one embodiment, system 10 is a CT system. In another embodiment, system 10 is a dual modality imaging system such as a combined CT/PET system and data can be processed in one modality (e.g., CT) and the processed data can be transferred to the other modality (e.g., PET). Display 20 can be separate from system 10 or integrated with system 10. System 10 includes an acquisition device such as an x-ray radiation detector 30.

Figure 2:
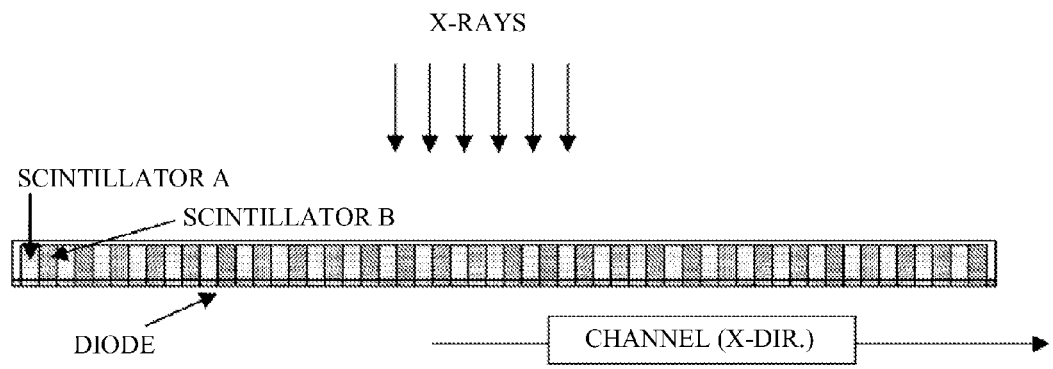
FIG. 2 illustrates one embodiment, using two types of scintillators.

The detector 30 can be built in different ways. FIG. 2 illustrates one embodiment, using two types of scintillators. In this configuration, one can imagine using just two different scintillating materials from one channel to another. The scintillating material for odd channels can be chosen to be spectrally different from the material of the even channels. In this case, combined with an appropriate focal spot deflection in x-direction, one can acquire the projection from both scintillators in one rotation. It is contemplated that the benefits of the invention accrue to embodiments with more than two different scintillator materials. For example, 3, 4, or 5 different interleaved channels of different scintillating materials could be done.

Figure 3:
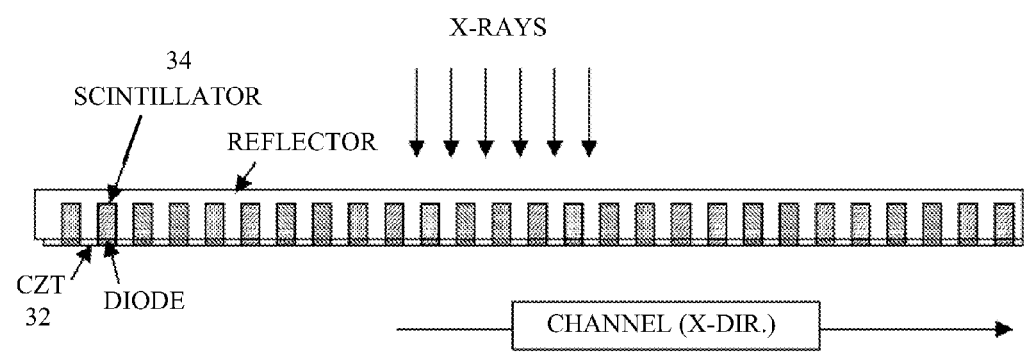
FIG. 3 illustrates that the detector can be built in different ways, and, more specifically.

FIG. 3 illustrates that the detector 30 can be built in different ways, and more specifically FIG. 3 illustrates a detector with a CDM detector portion 32 and a scintillator portion 34.

In this configuration, one can imagine using two different detectors and materials composing the channels, mixing photon counting detector and a scintillator type detector. One can imagine, the odd channels to be composed of photon counting detector such as using CDM only and the even channels to be integrating detectors based on scintillators (conventional detectors). In this case, combined with an appropriate focal spot deflection in the x-direction, one can acquire the projection data from both scintillators and CDM detectors in one rotation, and with the right in-plane resolution.

Figure 4:
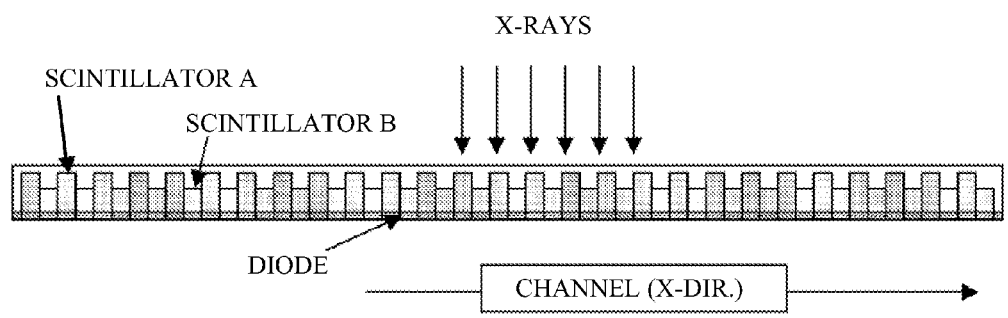
FIG. 4 illustrates again that the detector may be built in different manners and, more particularly.

FIG. 4 illustrates again that the detector 30 may be built in different manners and, more particularly, FIG. 4 illustrates a detector with different thicknesses of scintillator material.

In this configuration, one can imagine using the same scintillating material, from one channel to another but with different thickness. The scintillating material for odd channels can be chosen to be shorter or longer than the material of the even channels to achieve a significant difference in the spectral response from each. In this case, combined with the appropriate focal spot deflection in the x-direction, one can acquire the projection data from both scintillators in one rotation with different spectral content.

Figure 5:
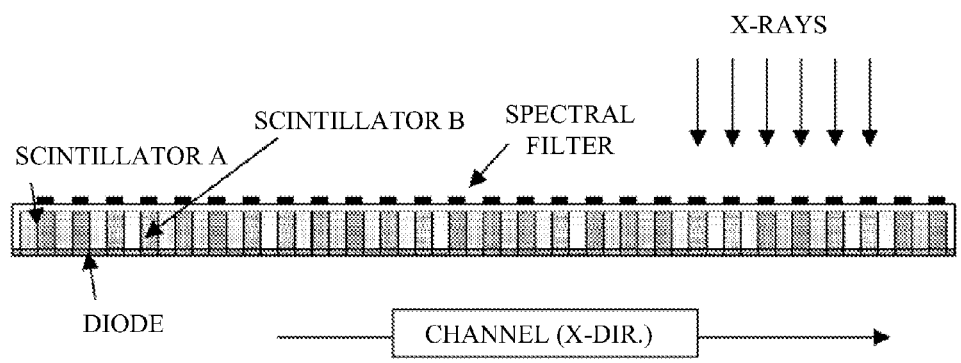
FIG. 5 illustrates again that the detector may be built in different manners and, more particularly.

FIG. 5 illustrates again that the detector 30 may be built in different manners and, more particularly, FIG. 5 illustrates a detector with a metallic filter on every other channel. Of course, the filter may not be metallic, any x-ray attenuating material may be used.

In this configuration, one can imagine using the same or different scintillating material, from one channel to another but with different spectral filtration from one channel to another. For example, a metallic filter to achieve a specific spectral window can cover the scintillating material for odd channels. The even channels can be left without a filter. Alternatively, filters can be used on all channels using different filter types on different channels. For example, one filter type can be used on the even channels and another filter type used on the odd channels. One commonality of all the embodiments described herein is that the channels are purposefully different from each other in some respect other than being different channels. In this case, combined with the appropriate focal spot deflection in x-direction, one can acquire the projection data from both scintillators in one rotation with different spectral windows. Additionally all the above described ways to differentiate the channels may be combined in all manners. For example different scintillating material can be used for the scintillators at different heights and a filter can be used with them. Additionally it is contemplated that they are could be other ways to differentiate one channel from another, and these un-described ways are not meant to be excluded.

Technical effects include that by using purposely different channels to obtain spectrally different data, one can perform at least one of a tissue differentiation and/or a material decomposition as is known in Energy Discrimination CT (EDCT).

Technical effects also include: (1) Energy discrimination using the same scintillator. (2) Energy discrimination by combining CDM detector and a scintillator. (3) Photon counting and obtaining an integrated signal at the same time. (4) Using the integrated signal to compensate or correct for the saturation of CDM detector under a high flux rate. (5) Calibrating the integrated signal to measure the flux rate. And, (6) using of the same KV to achieve the spectral discrimination. In other words during a scan the x-ray tube KV is maintained constant, but the effect of changing the x-ray tube KV is obtained by using at least two channels that are different.

The x-ray imaging system 10 includes a processing circuit 12. The processing circuit 12 (e.g., a microcontroller, microprocessor, custom ASIC, or the like) is coupled to a memory 14 and a display device 20. The memory 14 (e.g., including one or more of a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, or an other digital source such as a network or the Internet, as well as yet to be developed digital means, and the like) stores imaging data.

The memory 14 may also store a computer program including instructions executed by the processing circuit to implement the functions described herein. The processing circuit 12 provides an image for display on a device 20. The detector 30 may be a flat panel solid state image detector, for example, although conventional film images stored in digital form in the memory may also be processed. In one embodiment, the processing circuit 12 executes instructions stored in firmware (not shown).

Of course, the methods described herein are not limited to practice in system 10 and can be utilized in connection with many other types and variations of imaging systems. In one embodiment, the processing circuit 12 is a computer that is programmed to perform functions described herein, and, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a human patient setting, it is contemplated that the benefits of the invention accrue to non-human imaging systems such as those systems typically employed in small animal research.

Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A non-transitory computer readable medium having a computer program stored thereon and representing a set of instructions that when executed by a computer causes the computer to:
   cause an x-ray source to emit x-rays toward different portions of an x-ray detector, wherein one portion of the x-ray detector comprises a plurality of detector cells having a first spectral property, and wherein another portion of the x-ray detector comprises a plurality of detector cells having a second spectral property;
   acquire two sets of projection data of a given plane from the two different portions of the x-ray detector during a common rotation of the x-ray detector;
   cause the x-ray source to emit x-rays in an alternating pattern between a detector cell of the first spectral property and a detector cell of the second spectral property along a length of the x-ray detector; and
   create an image from the two sets of projection data, wherein the detector cells of the first spectral property and the detector cells of the second spectral property are interleaved along the length of the x-ray detector.

2. The computer readable medium of claim 1 further configured to cause the computer to perform one of focal spot deflection and an interpolation algorithm to acquire the two sets of projection data.

3. The computer readable medium of claim 1 further configured to cause the computer to:
   acquire one set of projection data from a plurality of scintillator cells; and
   acquire another set of projection data from a plurality of direct conversion material (CDM) detector cells.

4. The computer readable medium of claim 1 further configured to cause the computer to:
   acquire one set of projection data from a plurality of filtered detector cells; and
   acquire another set of projection data from a plurality of unfiltered detector cells.

5. The computer readable medium of claim 1 further configured to cause the computer to:
   acquire one set of projection data from a plurality of detector cells having a first cell height; and
   acquire another set of projection data from a plurality of detector cells having a second cell height.

6. A method comprising:
   emitting x-rays toward a first plurality of detector cells of an x-ray detector, the first plurality of detector cells having a first spectral property;
   emitting x-rays toward a second plurality of detector cells of the x-ray detector, the second plurality of detector cells having a second spectral property;
   acquiring a first set of image data and a second set of image data during the same rotation of the x-ray detector, wherein the first set of image data is acquired from the first plurality of detector cells, and wherein the second set of image data is acquired from the second plurality of detector cells;
   generating a common image using both the first and second sets of image data; and
   wherein acquiring the first and second sets of image data comprises performing one of focal spot deflection and an interpolation algorithm, wherein the first plurality of detector cells and the second plurality of detector cells are interleaved along a length of the x-ray detector.

7. The method of claim 6 further comprising emitting x-rays from a single KV source.

8. The method of claim 6 further comprising generating an energy discriminating image from the first set of image data and the second set of image data.

9. The method of claim 6 further comprising:
   emitting x-rays toward a plurality of scintillator detector cells; and
   alternately emitting x-rays toward a plurality of direct conversion material (CDM) detector cells.

10. The method of claim 6 further comprising:
    emitting x-rays toward a first plurality of detector cells having a first height; and
    alternately emitting x-rays toward a second plurality of detector cells having a second height.

11. The method of claim 6 further comprising:
    emitting x-rays toward a plurality of unfiltered detector cells; and
    alternately emitting x-rays toward a plurality of detector cells having x-ray attenuating filters.

12. A computed tomography (CT) imaging system comprising:
    an x-ray source configured to emit x-rays;
    a rotatable x-ray detector assembly having a plurality of detector cells positioned to receive x-rays emitted from the x-ray source, the rotatable x-ray detector comprising:
       a first plurality of detector cells having a first spectral property;
       a second plurality of detector cells having a second spectral property; wherein the first plurality of detector cells and the second plurality of detector cells are interleaved along a length of the x-ray detector; and
    a computer configured to:
       cause the x-ray source to emit x-rays toward the first plurality of detector cells;
       cause the x-ray source to emit x-rays toward the second plurality of detector cells;
       acquire a first set of projection data from the first plurality of detector cells;
       acquire a second set of projection data from the second plurality of detector cells, wherein the computer is configured to acquire the first and second sets of projection data during a given rotation of the rotatable x-ray detector assembly; and
       generate a single image using the first and second sets of projection data.

13. The CT imaging system of claim 12 wherein the computer is further configured to perform one of focal spot deflection and an interpolation to acquire the first and second sets of projection data.

14. The CT imaging system of claim 13 wherein the computer is configured to switch a focal spot in a channel direction of the CT imaging system.

15. The CT imaging system of claim 13 wherein the computer is configured to interpolate between one of channels and slices.

16. The CT imaging system of claim 12 wherein the first plurality of detector cells comprise scintillator cells; and
   wherein the second plurality of detector cells comprise direct conversion material (CDM) detector cells.

17. The CT imaging system of claim 12 wherein the first plurality of detector cells comprise filtered detector cells; and
   wherein the second plurality of detector cells comprise unfiltered detector cells.

18. The CT imaging system of claim 12 wherein the first plurality of detector cells comprise cells having a first thickness; and
   wherein the second plurality of detector cells comprise cells having a second thickness.

19. The CT imaging system of claim 12 wherein the computer is configured to generate an energy discriminating image from the first and second sets of projection data.

20. The CT imaging system of claim 12 wherein the first plurality of detector cells comprise a first scintillating material; and
   wherein the second plurality of detector cells comprise a second scintillating material.

* * * * *